US008882736B2

(12) United States Patent
Oliver

(10) Patent No.: US 8,882,736 B2
(45) Date of Patent: Nov. 11, 2014

(54) CONTAINER FOR RESUSPENDING SEDIMENTED MEDICAMENT

(75) Inventor: Martin Oliver, Cheshire (GB)

(73) Assignee: Norton Healthcare Limited, London (GB)

( * ) Notice: Subject to any disclaimer, the term of this patent is extended or adjusted under 35 U.S.C. 154(b) by 1520 days.

(21) Appl. No.: 11/994,239

(22) PCT Filed: Jun. 27, 2006

(86) PCT No.: PCT/GB2006/002367

§ 371 (c)(1),
(2), (4) Date: Apr. 18, 2008

(87) PCT Pub. No.: WO2007/003891

PCT Pub. Date: Jan. 11, 2007

(65) Prior Publication Data

US 2011/0196334 A1 Aug. 11, 2011

(30) Foreign Application Priority Data

Jul. 1, 2005 (GB) .................................. 0513581.9

(51) Int. Cl.

| | |
|---|---|
| ***A61B 19/00*** | (2006.01) |
| ***B01F 5/06*** | (2006.01) |
| ***B65D 1/02*** | (2006.01) |
| ***B01F 11/00*** | (2006.01) |
| ***B01F 13/00*** | (2006.01) |
| ***B65D 1/09*** | (2006.01) |
| ***A61J 1/06*** | (2006.01) |
| *B01F 3/00* | (2006.01) |
| *B01F 15/00* | (2006.01) |
| *B01F 3/12* | (2006.01) |

(52) U.S. Cl.

CPC ....... *B65D 1/0238* (2013.01); *B01F 2003/0028* (2013.01); *B01F 5/0661* (2013.01); *B01F 15/00506* (2013.01); *B01F 15/00512* (2013.01); *B01F 11/0005* (2013.01); *B01F 5/0666* (2013.01); *B01F 13/0022* (2013.01); *B01F 3/12* (2013.01); *B01F 13/002* (2013.01); *B65D 1/095* (2013.01); *A61J 1/067* (2013.01)

USPC .......................................... 604/403; 604/416

(58) Field of Classification Search

CPC ......... A61J 1/067; A61J 1/065; B65D 1/0238
USPC ...................... 604/403, 616; 215/48; 206/363
See application file for complete search history.

(56) References Cited

U.S. PATENT DOCUMENTS

| | | | | |
|---|---|---|---|---|
| 3,917,120 A * | 11/1975 | Larenz et al. | ................ | 222/129 |
| 5,009,894 A * | 4/1991 | Hsiao | ............................ | 424/451 |
| 5,380,534 A * | 1/1995 | Schurig et al. | ............... | 424/456 |
| 2002/0100741 A1 | 8/2002 | Weiler | | |
| 2004/0253039 A1 * | 12/2004 | Stenton | ......................... | 401/132 |

FOREIGN PATENT DOCUMENTS

| | | |
|---|---|---|
| EP | 0734955 | 10/1996 |
| EP | 0743057 | 11/1996 |
| EP | 0745369 | 12/1996 |
| EP | 1133969 | 9/2001 |
| GB | 823155 | 11/1959 |
| GB | 2079238 | 1/1982 |
| WO | WO2004039369 | 5/2004 |

* cited by examiner

OTHER PUBLICATIONS

International Search Report Corresponding to International Application No. PCT/GB2006/002367 dated Aug. 25, 2006.

*Primary Examiner* — Leslie Deak

(74) *Attorney, Agent, or Firm* — RatnerPrestia

(57) ABSTRACT

A container for re-suspending sedimented medicament comprises a reservoir for containing a suspension of particles in a liquid, a dispensing portion, and a sealing portion. The sealing portion is arranged to be in fluid communication with the reservoir via an orifice. The orifice is positioned between the dispensing portion and the sealing portion, and allows a turbulent flow of the liquid from the reservoir into the sealing portion to enable re-suspension of particles that have sedimented out of the liquid in the sealing portion.

18 Claims, 4 Drawing Sheets

CONTAINER FOR RESUSPENDING SEDIMENTED MEDICAMENT

This application is the U.S. national phase application of PCT International Application No. PCT/GB2006/002367, filed Jun. 27, 2006, which claims priority to GB Patent Application No. 0513581.9, filed Jul. 1, 2005, which are incorporated herein by reference.

FIELD OF THE INVENTION

The present invention relates to a container for storing and dispensing a suspension. In particular, the suspension is a suspension of a medicament, for example, a glucocorticosteroid.

BACKGROUND OF THE INVENTION

Many medicaments take the form of a suspension of particles in a carrier liquid. Typically the size of a medicament particle is less than 10 micrometers. An example of such a particle is a glucocorticosteroid particle.

These suspensions are often sterile and are stored in containers made from polymeric materials having thermoplastic properties that allow them to be easily moulded into appropriate shapes for storage containers.

Typically the storage container is shaped to allow easy dispensing of the medicament from the container by squeezing the container. The dispensing of the medicament is usually achieved by manually squeezing the container so that the container is deformed. The increased pressure in the container forces the liquid out of the container through an opening.

EP1133969 discloses a container for liquid or pasty substances or powders, suspensions or liposomial preparations, for pharmaceuticals, diagnostics, cosmetics or similar, enclosed in a plate of plastic material, comprising two semi-containers with bodies and necks, close together and parallel. Pre-cut lines are provided and at least some of these concern the said necks, in such a way as making a separation along these pre-cut lines causes the selective opening of a semi-container, or of both of them, and therefore the dispensing of a half dose or of the entire dose of the product in the container. A set of containers is also described, comprising a plurality of containers joined between themselves along lines of breakable joints and that allow their separation at the moment of use.

WO2004/039369 relates to a single-use container for a topically applied medicament or cosmetic agent, comprising a single dose of melatonin or melatonin derivative, which corresponds to a locally effective dose but does not have any systemic effect.

EP0743057 discloses a soft gelatin capsule containing a medicament and comprises a flexible hollow shell having a bulb with a tampered section leading to a removal tab integrally formed therewith, the junction between the tab and the tapered section defines an expulsion port. The bulb is in the form of any elongate body having top and bottom flattened portions which portions are provided with knurled texture regions.

GB2079238 disclosed a container made of low-density polyethylene coated on at least one side with a sealant film having an outlet which is closed by a closure tab which can be permanently separated from the remainder of the container along a weakened portion for dispensing one dose of medicament such as 0.5 to 5 g of an anti-inflammatory steroid formulation contained therein. A plurality of such containers can be connected at the tab and/or body to form a strip. The film, which may be derived from cellulose, an acrylic resin, or polyvinyl chloride, is formed by coating with a solution, dispersion or foam of the polymer is a suitable medium after pre-treating the substrate polyethylene by corona discharge, ionizing radiation, or an oxidizing agent. The coating operation is preferably performed after filling and closing the containers.

GB823155 discloses a sterile, single-dose, multiple-unit package of medicament, and a method for making the same.

Frequently the storage container will not be used immediately by the pharmacist, hospital or patient so it is necessary to store the container for an extended period of time. Storage of suspensions in such containers frequently leads to settling of the particles out of the carrier liquid and deposition on the container walls. The suspension may settle in such a way that it is not easily re-suspended by gentle shaking or flicking the container with, for example, a finger.

If the container is stored upright, i.e. the base of the container downwards, the particles will settle at the base of the container and may be easily re-suspended by the user prior to use. However, frequently the container is inadvertently stored in an inverted orientation, i.e. the dispensing portion and orifice is downwards. Consequently the particles settle in the dispensing portion near the orifice. Re-suspension of the sedimented particles is made difficult because of the narrowed cylindrical and/or tapered shape of the dispensing portion that is frequently used by manufacturers. The narrowed cylindrical tapering shape of the dispensing portion acts to restrict the free flow of the medicament in the dispensing portion. The narrowed tapering shape also restricts the ability of the medicament to form a vortex, or other type of turbulent flow, which will dislodge the sedimented particles from the wall, at or near the distal end (orifice end) of the dispensing portion. This may be due to, amongst other factors, a surface tension effect in the dispensing portion near the orifice. Re-suspension may require multiple inversions and repeated flicking of the container in order to detach the particles from the container walls. Agglomeration of the particles into clumps of particles comprising multiple particles is also a problem.

This settling, and subsequent inadequate re-suspension, reduces the effective amount of the medicament that is suspended in the carrier liquid. Consequently the effective dose that a patient will receive when the suspension is dispensed from the container is also reduced. If the size of the particle is crucial to the delivery of the medicament to the affected site in the patient, e.g. inhaled glucocorticosteroids in asthma patient's lungs, then disintegration of clumps of particles is important. If the patient is old, weak, or impatient it is more likely that they will be unable to effectively re-suspend the particles into the suspension or will inadequately re-suspend the particles. In both cases the patient will receive a reduced, or variable, dose of the medicament. Such a dose may be inadequate for the patients needs.

SUMMARY OF THE INVENTION

According to an embodiment of the invention, re-suspension of sedimented particles is facilitated.

An embodiment of the present invention provides a container comprising a reservoir containing a suspension of particles in a liquid, a dispensing portion and a sealing portion, said sealing portion is arranged to be in fluid communication with the reservoir via an orifice, said orifice is positioned between the dispensing portion and the sealing portion and allows flow of the liquid from the reservoir into the sealing portion to enable re-suspension of particles that have sedimented out of the liquid in the sealing portion.

Further preferred features and advantages of the invention are recited in the detailed description and in the claims.

BRIEF DESCRIPTION OF THE DRAWINGS

An embodiment of the invention will now be described, by way of example, with reference to the accompanying figures.

DETAILED DESCRIPTION OF THE PREFERRED EMBODIMENTS

The present invention provides a compressible thermoplastic container that allows easy re-suspension of particles that have settled out of a suspension during storage.

Figure 1:
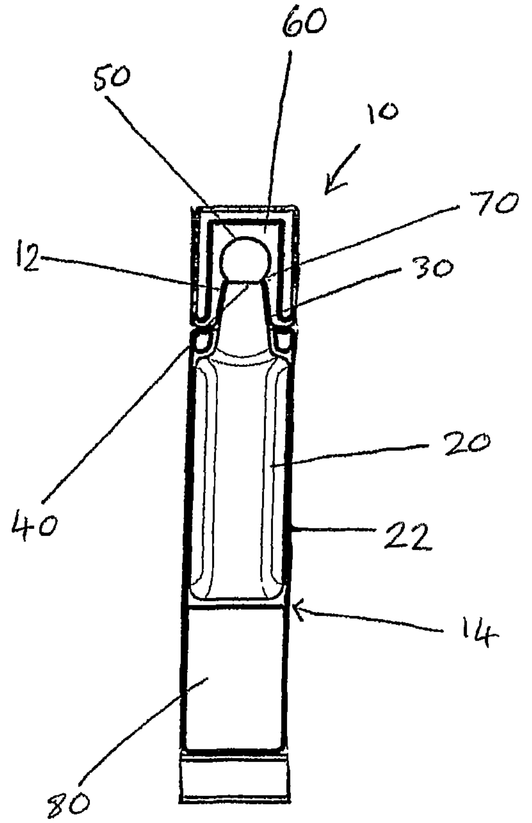
FIG. 1 shows a plan view of a representation of a container according to the invention.

FIG. 1 shows a representation of a container 10 having a reservoir 20 and a dispensing portion 30, the dispensing end 12 of dispensing portion 30 has an orifice 40. The reservoir 20 is sealed by the sealing portion 50. The sealing portion 50 is provided with a holding tab 60. The reservoir 20 is in fluid communication with the sealing portion 50 via the orifice 40. A transition portion 70 is between the dispensing portion 30 and the sealing portion 50. An identification tab 80 is formed integrally with the container 10 at the base end 14 of the container 10.

Typically the reservoir 20 is polygonal in cross-section but any shape that allows the user to exert opposing compression forces on the sides of the container 10 is envisaged. Appropriate shapes are known to the person skilled in the art and include polygonal shapes including square, rectangular and circular cross-sectioned reservoirs 20.

The container 10 is symmetrical in relation to two longitudinal planes and is, for example, molded in two halves. Typically the polymeric material has thermoplastic properties allowing the container 10 to be formed in a heated mould, for example, by injection molding. Alternative methods of forming the container are known to the person skilled in the art.

In order to allow squeezing of the container, and discharge of the contents, the walls of the container must be thin enough to allow them to be compressed using manual strength but also thick enough to protect the medicament from the environment, for example, from puncturing by sharp external objects or diffusion of oxygen through the walls of the container. This is especially important when the medicament is sterile.

Usually the thickness of the container wall 22 is about 0.5 to about 1.0 mm so as to allow easy compression of the container 10. The range of container wall thicknesses appropriate for such use is known to the person skilled in the art or can be determined without undue experimentation or the exercise of inventive skill.

Typically the reservoir 20 holds a volume of about 0.1 to about 15 ml. Preferably the volume of the reservoir 20 is about 0.1 to about 10 ml. More preferably, the volume is about 0.1 to about 5 ml. The container wall 22 may comprise graduations that allow the user to dispense a measured volume of medicament. If desired, the container 10 can contain a volume of medicament sufficient for two or more dosages.

Typically the medicament is a suspension of particles. These particles may be glucocorticosteroids if the medicament is to be used for the treatment of pulmonary diseases, including asthma and chronic obstructive pulmonary disease.

The term "glucocorticosteroids" refers to any of a group of steroid hormones (including derivatives, synthetic analogs, and pro-drugs), such as cortisone, which are produced by the adrenal cortex. These compounds are involved in carbohydrate, protein, and fat metabolism. The glucocorticosteroids may have anti-inflammatory properties.

The glucocorticosteroids are preferably anti-inflammatory glucocorticosteroids. Non-limiting examples of glucocorticosteroids, which may be used in the present invention, include beclamethasone, budesonide, ciclesonide, cotivazol, deflazacort, flumetasone, flunisolide, flucinolone, fluticasone, mometasone, rofleponide, tipredane and triamcinolone. Preferably the glucocorticosteroid is budesonide, beclamthasone, ciclesonide, fluticasone, mometasone and triamcinolone. Most preferably, the glucocorticosteroid is budesonide and beclamethasone.

Alternatively the suspension may be a suspension of vaccine particles such as dead or attenuated bacteria, fungi, protozoa or virus, or other such particles as are known to be appropriate. The suspension may comprise more than one medicament. For example, the medicaments may be different glucocorticosteroids. In some embodiments, the second active ingredient may be selected from albuterol, ipratropium, bromide, formoterol, tiotropium, oxitropium and azelastine.

The medicaments of the invention may conveniently be presented in unit dosage form and may be prepared by conventional pharmaceutical techniques. The medicaments of the invention may be sterile. The sterile glucocorticosteroid may be used in the treatment of allergic and/or inflammatory conditions. The allergic and/or inflammatory condition may not be restricted to one site, e.g. the nose or lungs. Allergic and/or inflammatory conditions include, without limitation, contact dermatitis, asthma, rhinitis, or chronic obstructive pulmonary disease.

Usually the container 10 is manufactured from a polymeric material selected from the group comprising, for example, polyethylene, polypropylene or polyester or other such materials that are known by the person skilled in the art to be appropriate for the manufacture of containers according to the invention. The container material may be selected so that it does not react with the medicament.

A property of the polymeric material is that it is deformable to allow the container 10 to deform when squeezed. The reservoir 20 is typically deformed by squeezing between two or more fingers or a thumb and two or more fingers. For example, the thumb or a finger may be on one side and another finger on the opposing side, or face, of the reservoir 20. By squeezing the reservoir 20 the medicament is forced towards the dispensing portion 30 of the container 10 and the orifice 40.

Desirably the dispensing portion 30 is substantially conical, preferably frusto-conical, although other shapes known to the person skilled in the art as being appropriate may be used. The dispensing portion 30 may taper to allow the accurate formation, and dispensing, of drops of a known volume.

The orifice 40 is arranged so that it allows flow of the medicament into the sealing portion 50 from the reservoir 20 and re-suspension of particles that have settled in the sealing portion 50.

The diameter of the orifice 40 is from about 1 mm to about 6 mm. Preferably, the orifice 40 has a diameter of about 3 mm to about 4 mm. The size of the orifice 40 will typically be determined by the characteristics of the medicament e.g. viscosity, the volume of the reservoir 20 and the volume of the sealing portion 50.

The volume of the sealing portion 50 is between about 0.01 ml to about 1 ml. Preferably, the volume is about 0.1 ml to about 0.8 ml. More preferably, the volume is about 0.2 ml to about 0.6 ml. Most preferably, the volume is about 0.3 ml to about 0.5 ml. Typically the sealing portion 50 is spherical. Other shapes that allow the formation of a vortex in the medicament in the sealing portion 50 are envisaged, such shapes include an irregular spheroidal. The external diameter of the sealing portion 50 is from about 5 to about 15 mm. Preferably the diameter is about 7 mm. The size of the sealing portion 50 will typically be determined by the type of medicament, its usage and the volume of the reservoir 20.

The wall of the transition portion 70 formed between the dispensing portion 30 and the sealing portion 50 is weaker than the wall of the dispensing portion 30 and the sealing portion 50. This weakening may be achieved, for example, by reducing the thickness of the container wall 22, or by scoring the container wall 22, or by other means known to the person skilled in the art. The transition portion 70 allows the sealing portion 50 to be easily detached from dispensing portion 30. When the sealing portion 50 is detached, the medicament may be dispensed from the dispensing portion 30 via the orifice 40.

The diameter of the transition portion 70 is from about 1 to about 12 mm.

The sealing portion 50 preferably has a holding tab 60 that allows the sealing portion 50 to be easily detached from the dispensing portion 30. The tab 60 allows the user to easily grip the sealing portion 50 and exert force upon the transition portion 70.

The container 10 may have an identification tab 80 that allows information relating to the batch number, type of medicament or expiry date to be presented to the user. The information may be embossed or printed onto the identification tab.

Figure 2:
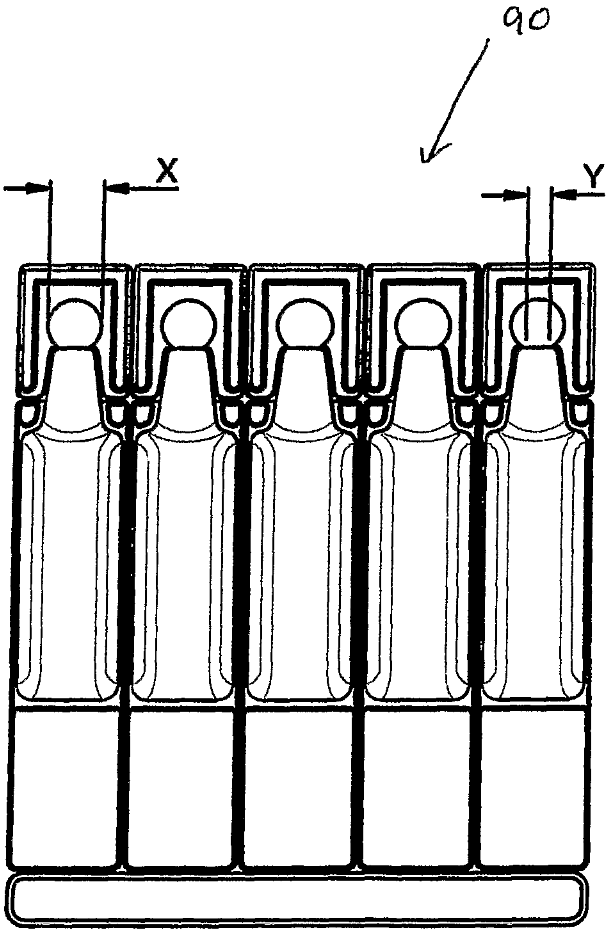
FIG. 2 shows a plan view of a representation of a pack of containers according to the invention.
Figure 3:
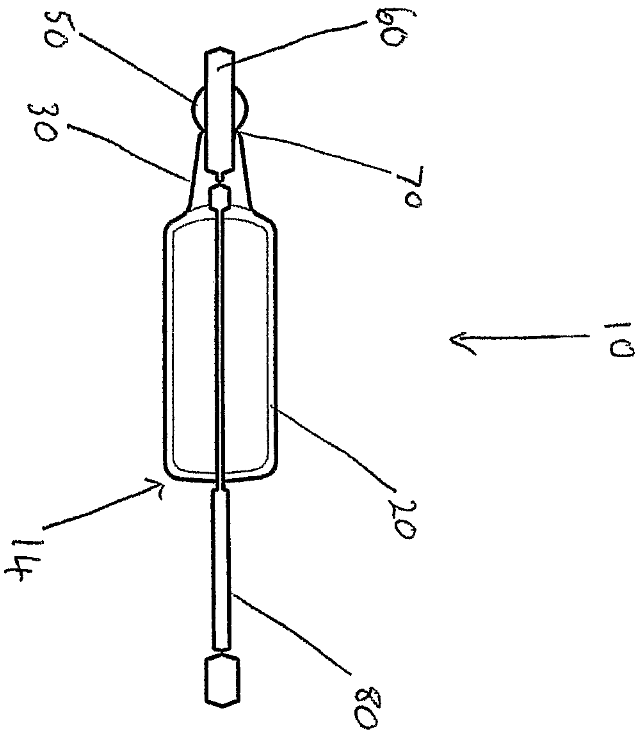
FIG. 3 shows a side view of a representation of a container according to the invention.
Figure 4:
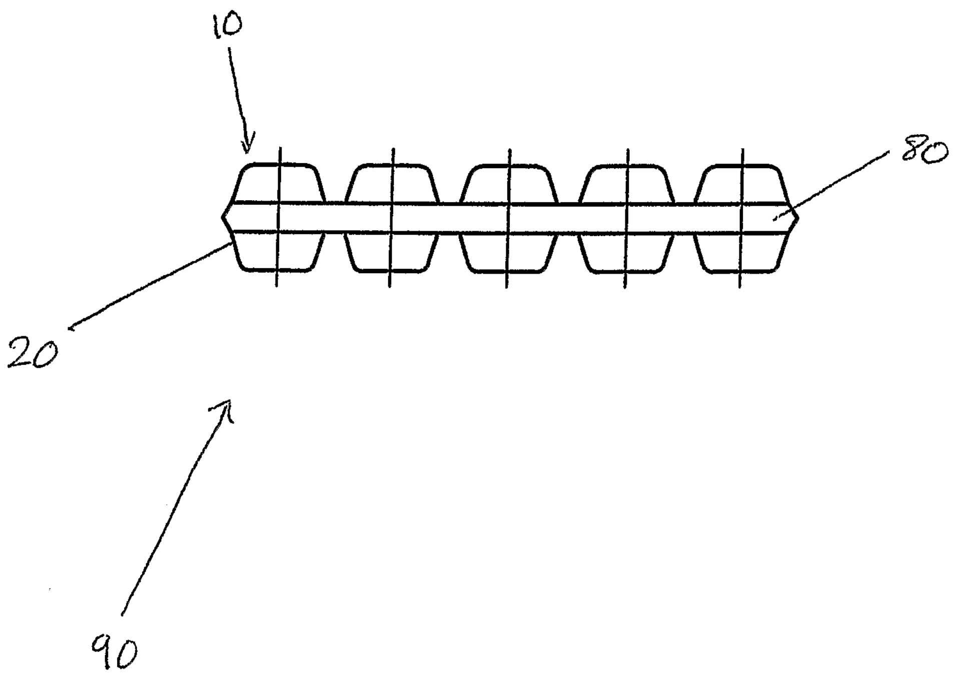
FIG. 4 shows a view of the base of a representation of a container according to the invention.

Two or more containers 10 may be connected together to form a pack of containers 90 (as shown in FIG. 2). This allows the dispensing of a course of treatment to a user. The type of medicament contained in the containers 10 may be identical or they may be different medicaments.

The following examples are intended to further illustrate certain embodiments of the invention, and are not limiting in nature. Those skilled in the art will recognize, or be able to ascertain, using no more than routine experimentation, numerous equivalents to the specific examples described herein.

EXAMPLES

Example 1

Containers according to the invention containing budesonide inhalation suspension at the concentration shown were stored in an inverted position for 24 hours. Following storage the containers were gently shaken and the amount of sediment that could not be easily re-suspended was determined by drying the sealing portion and weighing the sediment remaining. Suspension steri-neb represents a container according to the invention.

Results for 1.0 mg/2 ml vials after 24 hours storage inverted.

| Content in mg/vial | | | | | |
|---|---|---|---|---|---|
| | Vial No. | | | | |
| | 1 | 2 | 3 | 4 | 5 |
| Suspension steri-neb | 0.013 | 0.026 | 0.013 | 0.011 | 0.013 |
| Standard Steri-neb | 0.27 | 0.326 | 0.036 | 0.147 | 0.235 |

| Content in % of theoretical content (1.0 mg/2 ml) | | | | | |
|---|---|---|---|---|---|
| | Vial No. | | | | |
| | 1 | 2 | 3 | 4 | 5 |
| Suspension steri-neb | 1.3 | 2.6 | 1.3 | 1.1 | 1.3 |
| Standard Steri-neb | 27 | 32.6 | 3.6 | 14.7 | 23.5 |

Example 2

Containers according to the invention containing budesonide inhalation suspension at the concentration shown were stored in an inverted position for 24 hours. Following storage the containers were gently shaken and the amount of sediment that could not be easily re-suspended was determined by drying the sealing portion and weighing the sediment remaining. Suspension steri-neb represents a container according to the invention.

Results for 0.25 mg/2 ml vials after 24 hours storage inverted.

| Content in mg/vial | | | | | |
|---|---|---|---|---|---|
| | Vial No. | | | | |
| | 1 | 2 | 3 | 4 | 5 |
| Suspension steri-neb | 0.008 | 0.01 | 0.005 | 0.006 | 0.005 |
| Standard Steri-neb | 0.069 | 0.016 | 0.006 | 0.02 | 0.022 |

| Content in % of theoretical content (0.25 mg/2 ml) | | | | | |
|---|---|---|---|---|---|
| | Vial No. | | | | |
| | 1 | 2 | 3 | 4 | 5 |
| Suspension steri-neb | 3.2 | 4 | 2 | 2.4 | 2 |
| Standard Steri-neb | 27.6 | 6.4 | 2.4 | 8 | 8.8 |

The invention claimed is:

1. A compressible thermoplastic container comprising:

a body having a constant width along a length dimension of the body, said body including:

(a) a reservoir containing a suspension of particles in a liquid, (b) a dispensing portion of the reservoir, (c) a sealing portion positioned at one end of the reservoir, wherein said sealing portion is arranged to be in fluid communication with the reservoir via an orifice, said orifice being positioned between the dispensing portion and the sealing portion, and allowing flow of the liquid from the reservoir into the sealing portion when the container is inverted; and (d) a holding tab at least partially surrounding and attached to the sealing portion and the dispensing portion, wherein the sealing portion has a spheroidal shape and volume that allows for the formation of a vortex in said suspension flowing into the sealing portion, sufficient to resuspend particles that have sedimented out of the liquid in the sealing portion.

2. A container according to claim 1, wherein the flow in the sealing portion is turbulent flow.

3. A container according to claim 1, wherein the flow in the sealing portion is the formation of a vortex.

4. A container according to claim 1, wherein the diameter of the orifice is from about 1 mm to about 6 mm.

5. A container according to claim 4, wherein the diameter of the orifice has a diameter of about 3 mm.

6. A container according to claim 1, wherein the sealing portion is spherical.

7. A container according to claim 1, wherein the container comprises a transition portion between the dispensing portion and the sealing portion that allows a user to easily detach the sealing portion from the dispensing portion.

8. The container according to claim 1 further comprising information disposed on an identification tab positioned at an opposing end of the reservoir pertaining to batch number, type of medicament or expiry date.

9. A compressible thermoplastic container comprising:

a body having a constant width along a length dimension of the body, said body including:

(a) a container wall defining a reservoir, wherein the reservoir is adapted to contain a suspension of particles in a liquid;

(b) a dispensing portion of the reservoir;

(c) a sealing portion positioned at one end of the reservoir which is in fluid communication with the reservoir via an orifice, wherein the orifice is disposed between the dispensing portion and the sealing portion, wherein the container is adapted to allow a flow of the liquid from the reservoir into the sealing portion when the container is inverted; and (d) a holding tab at least partially surrounding and attached to the sealing portion and the dispensing portion, wherein the sealing portion has a spheroidal shape and volume that allows for the formation of a vortex in said suspension to enable re-suspension of particles that sediment out of the liquid in the sealing portion.

10. The container according to claim 9, wherein the reservoir contains a suspension of particles in a liquid.

11. The container according to claim 10, wherein the flow of liquid in the sealing portion is a turbulent flow.

12. The container according to claim 10, wherein the flow of liquid in the sealing portion is a vortex.

13. The container according to claim 12, wherein the diameter of the orifice is about 3 mm.

14. The container according to claim 9, wherein the orifice has a diameter of between about 1 mm to about 6 mm.

15. The container according to claim 9, wherein the sealing portion is spherical.

16. The container according to claim 9 further comprising a transition portion disposed between the dispensing portion and the sealing portion for allowing a user to detach the sealing portion from the dispensing portion.

17. The container according to claim 9 further comprising a base end, wherein an identification tab positioned at an opposing end of the reservoir is formed integrally with the container at the base end.

18. The container according to claim 9 further comprising information disposed on an identification tab positioned at an opposing end of the reservoir pertaining to batch number, type of medicament or expiry date.

* * * * *